(12) United States Patent
Hosokawa et al.

(10) Patent No.: US 11,142,787 B2
(45) Date of Patent: Oct. 12, 2021

(54) METHOD FOR PERFORMING SINGLE-CELL ANALYSIS AND DEVICE THEREFOR

(71) Applicant: bitBiome, Inc., Tokyo (JP)

(72) Inventors: Masahito Hosokawa, Tokyo (JP); Haruko Takeyama, Tokyo (JP); Yohei Nishikawa, Tokyo (JP); Masato Kogawa, Tokyo (JP)

(73) Assignee: bitBiome, Inc., Tokyo (JP)

( * ) Notice: Subject to any disclaimer, the term of this patent is extended or adjusted under 35 U.S.C. 154(b) by 0 days.

(21) Appl. No.: 17/053,622

(22) PCT Filed: Apr. 26, 2019

(86) PCT No.: PCT/JP2019/017952
§ 371 (c)(1),
(2) Date: Nov. 6, 2020

(87) PCT Pub. No.: WO2019/216271
PCT Pub. Date: Nov. 14, 2019

(65) Prior Publication Data
US 2021/0246495 A1    Aug. 12, 2021

(30) Foreign Application Priority Data

May 7, 2018   (JP) ............................. JP2018-089259

(51) Int. Cl.
| C12Q 1/6848 | (2018.01) |
| C12N 15/10 | (2006.01) |
| C12N 11/04 | (2006.01) |
| B01L 3/00 | (2006.01) |

(52) U.S. Cl.
CPC ...... *C12Q 1/6848* (2013.01); *B01L 3/502792* (2013.01); *C12N 11/04* (2013.01); *C12N 15/10* (2013.01); *C12N 15/1093* (2013.01); *B01L 2200/0652* (2013.01); *B01L 2200/0663* (2013.01)

(58) Field of Classification Search
None
See application file for complete search history.

(56) References Cited

U.S. PATENT DOCUMENTS

2011/0159499 A1   6/2011   Hindson et al.

FOREIGN PATENT DOCUMENTS

| JP | 2013-511991 A | 4/2013 |
| JP | 2017-532024 A | 11/2017 |
| WO | 2011/066476 A1 | 6/2011 |
| WO | 2015/069798 A1 | 5/2015 |
| WO | 2016/040476 A1 | 3/2016 |
| WO | 2017/218486 A1 | 12/2017 |
| WO | 2018/043533 A1 | 3/2018 |

OTHER PUBLICATIONS

Kumaresan et al., "High-Throughput Single Copy DNA Amplification and Cell Analysis in Engineered Nanoliter Droplets," *Anal. Chem.* 80:3522-3529, 2008.
Ling et al., "Evaluation of genome coverage and fidelity of multiple displacement amplification from single cells by SNP array," *Molecular Human Reproduction* 15(11):739-747, 2009.
Novak et al., "Single-Cell Multiplex Gene Detection and Sequencing with Microfluidically Generated Agarose Emulsions," *Angew. Chem. Int. Ed.* 50:390-395, 2011.
Xu et al., "Single-Cell Exome Sequencing Reveals Single-Nucleotide Mutation Characteristics of a Kidney Tumor," *Cell* 148:886-895, 2012.
Zhang et al., "Massively Parallel Single-Molecule and Single-Cell Emulsion Reverse Transcription Polymerase Chain Reaction Using Agarose Droplet Microfluidics," *Anal. Chem.* 84:3599-3606, 2012.
Hosokawa et al., "Massively parallel whole genome amplification for single-cell sequencing using droplet microfluidics," *Scientific Reports* 7:5199, DOI:10.1038/s41598-017-05436-4, 2017, 11 pages.
Lan et al., "Single-cell genome sequencing at ultra-high-throughput with microfluidic droplet barcoding," *Nature Biotechnology* 35(7), 2017, 11 pages.
Tamminen et al., "Single gene-based distinction of individual microbial genomes from a mixed population of microbial cells," *Frontiers in Microbiology* 6(195), 2015, 10 pages.
Xu et al., "Virtual microfluidics for digital quantification and single-cell sequencing," *Nature Methods* 13(9), 2016, 6 pages.
Lam et al., "Loop-mediated isothermal amplification of a single DNA molecule in polyacrylamide gel-based microchamber," *Biomed Microdevices* 10:539-546, Feb. 2008.
Mazutis et al., "Droplet-Based Microfluidic Systems for High-Throughput Single DNA Molecule Isothermal Amplification and Analysis,"*Anal. Chem,* 81:4813-4821, Jun. 2009.
Nikodinovic et al., "High yield preparation of genomic DNA from Streptomyces," *BioTechniques* 35:932-936, Nov. 2003.
Zanoli et al., "Isothermal Amplification Methods for the Detection of Nucleic Acids in Microfluidic Devices," *Biosensors* 3:18-43, 2013.

*Primary Examiner* — Kaijiang Zhang
(74) *Attorney, Agent, or Firm* — Seed IP Law Group LLP

(57) ABSTRACT

The present invention provides a genome library production method in which cell lysis and genome amplification are performed using a simple operation. More particularly, the present invention provides a method that is for amplifying polynucleotides in cells and that comprises: a step for using a sample containing two or more cells or cell-like structures, and encapsulating the cells or cell-like structures into droplets, one for each droplet; a step for gelling the droplets to generate gel capsules; a step for performing lysis of the cells or cell-like structures by immersing the gel capsules in one or more types of reagents for lysis so as to cause the polynucleotides in the cells to be eluted in the gel capsules and to be kept in the gel capsules in a state where substances binding to the polynucleotides are removed; and a step for bringing the polynucleotides into contact with a reagent for amplification to amplify the polynucleotides in the gel capsules.

21 Claims, 5 Drawing Sheets

Specification includes a Sequence Listing.

SEQUENCE LISTING

```
<160> NUMBER OF SEQ ID NOS: 2

<210> SEQ ID NO 1
<211> LENGTH: 50
<212> TYPE: DNA
<213> ORGANISM: artificial sequence
<220> FEATURE:
<223> OTHER INFORMATION: Forward Primer
<220> FEATURE:
<221> NAME/KEY: misc_feature
<222> LOCATION: (42)..(42)
<223> OTHER INFORMATION: n is a, c, g, t or u

<400> SEQUENCE: 1
tcgtcggcag cgtcagatgt gtataagaga cagcctacgg gnggcwgcag              50

<210> SEQ ID NO 2
<211> LENGTH: 55
<212> TYPE: DNA
<213> ORGANISM: artificial sequence
<220> FEATURE:
<223> OTHER INFORMATION: Reverse Primer

<400> SEQUENCE: 2
gtctcgtggg ctcggagatg tgtataagag acaggactac hvgggtatct aatcc        55
```

METHOD FOR PERFORMING SINGLE-CELL ANALYSIS AND DEVICE THEREFOR

STATEMENT REGARDING SEQUENCE LISTING

The Sequence Listing associated with this application is provided in text format in lieu of a paper copy, and is hereby incorporated by reference into the specification. The name of the text file containing the Sequence Listing is 150171_401USPC_SEQUENCE_LISTING.txt. The text file is 790 bytes, was created on Nov. 2, 2020, and is being submitted electronically via EFS-Web.

TECHNICAL FIELD

The present invention relates to a method for performing single-cell analysis and a device for the same.

BACKGROUND ART

Analysis on each single cell in various biological samples containing a variety of cells is gradually becoming possible in recent years. However, such analysis still have several technical challenges in the sample preparation processes including effective separation of cells, lysis of a single cell, uniform amplification of the whole genome, quality assessment of a single cell amplified genome (SAG), preparation of a sequencing library, and sequencing analysis. For this reason, there is a significant demand for a novel technology that enables massively parallel analysis in order to maximize the quality and throughput.

Environmental microbes that can be cultured are limited to only 1% of environmental microbes. The vast majority of diversity in microbes on earth is unknown. Genome sequence information is basic information for understanding an organism. Genome sequencing enables understanding of the diversity and functions of microbes associated with the phylogeny, evolution, disease, or biogeochemical cycle. For this reason, whole genome analysis is considered indispensable for understanding the functions of uncultured microbes. The method used for such uncultured microbe genome analysis was mainly metagenomics that extracts various microbial genomes in bulk from a sample and determines the sequences.

However, a metagenomic method results in data containing information on genome sequences of various microbes. For this reason, genome information on a microbe of interest could not be readily extracted therefrom and reconstructed individually, requiring large-scale data acquisition and computation processes.

Meanwhile, single-cell analysis initiates processing after separating each cell at the beginning. Since only genetic information derived from a single cell is directly obtained, the complexity of computation for reconstructing genome information, for example, is dramatically simpler compared to metagenomic analysis. However, highly precise cell manipulation and nucleic acid reaction is required for completely determining a very small amount of genome sequence within a cell.

Steps of single-cell genome analysis can be roughly separated into (1) isolation of a single microbial cell, (2), lysis of the microbe, (3) whole genome amplification, and (4) sequence analysis of the amplified genome. However, a reaction system of tens of microliters used in conventional molecular biological experiments was unsuitable for precise handling of a very small sample, i.e., single cell, in accordance with the flow described above. Specifically, it was challenging to separate, recognize, and retrieve microbes from non-organism particles when isolating small and diverse microbes with non-uniform shapes by flow cytometry or the like. When handling isolated microbial samples, nucleic acids were frequently contaminated from the experimental environment, sample, or tester in a large capacity reaction system, and the yield for obtaining a normal amplicon is low, so that the vast majority of determined sequences were derived from an unrelated contamination in a very large number of cases.

Furthermore, the genome completeness was only about 30%, even from extracting only correct sequences by information processing. Since it is difficult to completely prevent contamination from aerosol or the like in an open experimental environment, a clean experimental environment dedicated to single-cell genome analysis experiments is required. The very low throughput of the reaction system in view of the need to execute sequencing from each one of the cells was also a problem, where an expensive isolation robot or the like was used in the experimental operations.

SUMMARY OF INVENTION

Solution to Problem

One aspect of the invention provides a method of amplifying a polynucleotide in a cell. The method can comprise the steps of: encapsulating two or more cells or cell-like structures in liquid droplets, at one cell or construct unit per liquid droplet, by using a sample comprising the cells or cell-like structures; converting the liquid droplets into gel to generate a gel capsule; immersing the gel capsule in one or more types of lysis reagents to lyse the cells or cell-like structures, wherein a polynucleotide in the cells, which has eluted out into the gel capsule, is retained in the gel capsule with a substance binding to the polynucleotide removed; and contacting the polynucleotide with an amplification reagent to amplify the polynucleotide within the gel capsule. Another aspect of the invention can provide a composition or device used in said method.

The method, composition, or device of the invention can be further specified to be those for genome sequencing of a cell at a single-cell level. The method, composition, or device of the invention can also be specified to bP those for preparation of a genome library.

Examples of embodiments of the invention include the following.
(Item A1)
A method of amplifying a polynucleotide in a cell or a cell-like construct, comprising the steps of:

encapsulating two or more cells or cell-like structures in liquid droplets, at one cell or construct unit per liquid droplet, by using a sample comprising the cells or cell-like structures;

converting the liquid droplets into gel to generate a gel capsule;

immersing the gel capsule in one or more types of lysis reagents to lyse the cells or cell-like structures, wherein a polynucleotide in the cells, which has eluted out into the gel capsule, is retained in the gel capsule with a substance binding to the polynucleotide removed; and contacting the polynucleotide with an amplification reagent to amplify the polynucleotide within the gel capsule.
(Item A2)

A method of genome sequencing of a cell at a single-cell level, comprising the step of determining a whole sequence of a genomic DNA of the cell from a polynucleotide amplified by the method of the preceding item.

(Item A3)

A method of preparing a genome library, comprising the step of sorting, separating, and collecting each gel capsule with the polynucleotide amplified by the method of any of the preceding items.

(Item A4)

The method of any of the preceding items, wherein the cells comprise a microbial cell.

(Item A5)

The method of any of the preceding items, wherein the lysis reagent and a contaminant are removed from the gel capsule after immersing the gel capsule in the lysis reagent.

(Item A6)

The method of any of the preceding items, wherein the liquid droplets encapsulating the cells or cell-like structures are prepared by allowing a suspension of the cells or cell-like structures to flow in a microchannel and shearing the suspension with oil.

(Item A7)

The method of any of the preceding items, wherein a diameter of the liquid droplets is 1 to 250 μm.

(Item A8)

The method of any of the preceding items, wherein a diameter of the gel capsule is 1 to 250 μm.

(Item A9)

The method of any of the preceding items, wherein the gel capsule is formed from agarose, acrylamide, photocurable resin, PEG, gelatin, sodium alginate, matrigel, or collagen.

(Item A10)

The method of any of the preceding items, wherein at least one type of the lysis reagent is selected from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12.

(Item A11)

The method of any of the preceding items, wherein the gel capsule is a hydrogel capsule.

(Item A12)

The method of any of the preceding items, wherein the step of amplifying is performed by a isothermal strand displacement amplification reaction.

(Item B1)

A device for amplifying a polynucleotide in a cell, comprising:

a liquid droplet preparation unit for encapsulating cells or cell-like structures in liquid droplets at one cell or construct unit per liquid droplet;

a gel capsule generation unit for converting the liquid droplets into gel to generate a gel capsule;

a lysis reagent immersion unit for immersing the gel capsule in a lysis reagent;

a removal unit for removing a contaminant from the gel capsule; and an amplification reagent immersion unit for immersing the gel capsule in an amplification reagent.

(Item B1-1)

The device of the preceding item, comprising a feature of any one or more of the preceding items.

(Item B2)

The device of any of the preceding items further characterized in genome sequencing of a cell at a single-cell level, further comprising a sequencing unit for sequencing a nucleic acid sequence in a polynucleotide amplified by the amplification reagent immersion unit.

(Item B3)

The device of any of the preceding items further characterized in preparing a genome library, further comprising a sorting unit for sorting the gel capsule and housing the gel capsule in a housing container.

(Item B4)

The device of any of the preceding items, wherein the liquid droplet preparation unit comprises a microchannel.

(Item C1)

A composition for amplifying a nucleic acid in a cell at a single-cell level, comprising a gel capsule or a material thereof.

(Item C2)

A composition for preparing a genome library, comprising a gel capsule or a material thereof.

(Item C3)

A composition for amplifying a nucleic acid in a cell at a single-cell level, comprising a gel capsule or a material thereof, and a cell in a single-cell state.

(Item C4)

A composition for preparing a genome library, comprising a gel capsule or a material thereof, and a cell in a single-cell state.

(Item C5)

A composition for sequencing a nucleic acid in a cell at a single-cell level, comprising a gel capsule or a material thereof, and a cell in a single-cell state.

(Item D1)

A composition for amplifying a nucleic acid in a cell at a single-cell level, comprising a lysis reagent, wherein the lysis reagent comprises at least one selected from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12.

(Item D1-1)

The composition of any of the preceding items, comprising a feature of one or more of any of the preceding items.

(Item E1)

A kit for amplifying a nucleic acid in a cell at a single-cell level, comprising a material of a gel capsule, and optionally one or more reagents.

(Item E2)

The kit of the preceding item, wherein the one or more reagents comprises a lysis reagent.

(Item E3)

The kit of any of the preceding items, wherein the lysis reagent comprises at least one selected from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12.

(Item E3-1)

The kit of any of the preceding items, comprising a feature of one or more of any of the preceding items.

The present invention is intended so that one or more of the features described above can be provided not only as the explicitly disclosed combinations, but also as other combinations thereof. Additional embodiments and advantages of the invention are recognized by those skilled in the art by reading and understanding the following detailed description as needed.

Advantageous Effects of Invention

The present invention can perform single cell analysis on individual cells in a cell population in a simple and convenient manner. In particular, the present invention can perform genome amplification and sequencing in a cell population at a single-cell level in a simple and convenient manner.

DESCRIPTION OF EMBODIMENTS

Figure 1:
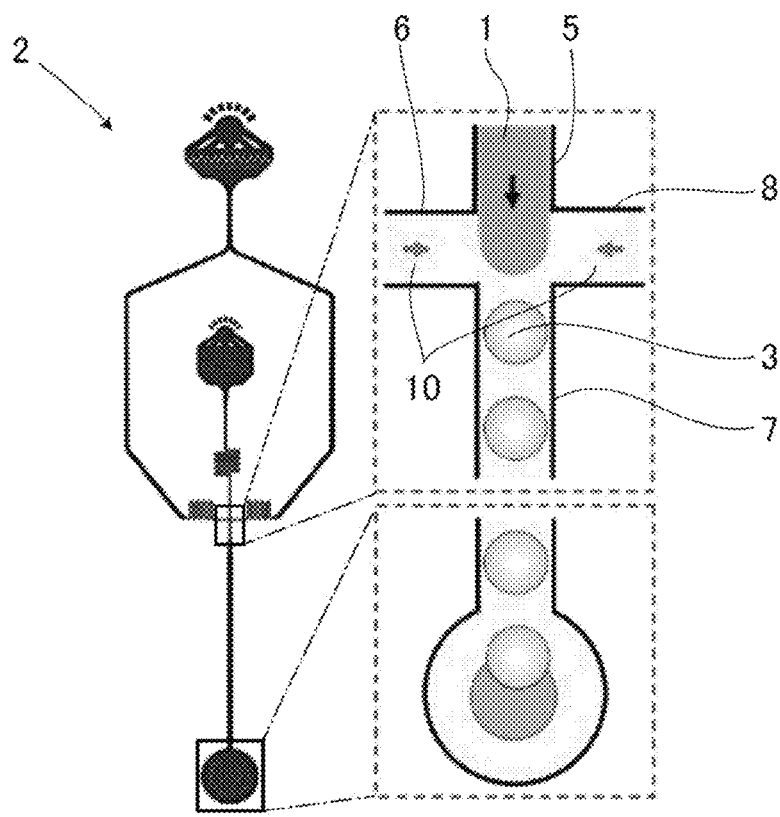
FIG. 1 is a diagram showing a microchannel of Example 1 of the invention.

The present invention is described hereinafter while showing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definitions

The definitions of the terms and/or basic technical matters especially used herein are described hereinafter when appropriate.

As used herein, "cell" refers to any particle containing a molecule with genetic information, which can be replicated (regardless of whether this is possible alone). The "cell" as used herein encompasses cells of a unicellular organism, bacteria, cells derived from a multicellular organism, fungi, and the like.

As used herein, "cell-like construct" refers to any particle containing a molecule with genetic information. The "cell-like construct" as used herein encompasses intracellular organelles, such as mitochondria, cell nuclei, and chloroplasts, viruses, and the like.

As used herein, "gel" refers to a colloidal solution (sol) wherein a polymeric substance or colloidal particles form a mesh structure as a whole due to the interaction thereof, and has lost fluidity while containing a large quantity of a liquid phase that is a solvent or dispersion medium. As used herein, "conversion into gel" refers to changing a solution into a state of "gel".

As used herein, "gel capsule" refers to a gel-like microparticulate construct that can retain a cell or cell-like construct therein.

As used herein, "genetic analysis" refers to studying the state of a nucleic acid (DNA, RNA, or the like) in a biological sample. In one embodiment, genetic analysis includes those that utilize a nucleic acid amplification reaction. Examples of genetic analysis include, in addition thereto, sequencing, genotyping/polymorphism analysis (SNP analysis, copy number variation, restriction fragment length polymorphism, repeat number polymorphism), expression analysis, Quenching Probe (Q-Probe), SYBR green method, melt curve analysis, real-time PCR, quantitative RT-PCR, digital PCR, and the like.

As used herein, "single-cell level" refers to processing of genetic information contained in a single cell or cell-like construct distinctly from genetic information contained in other cells or cell-like structures. For example, when a polynucleotide is amplified at a "single-cell level", a polynucleotide in a cell and a polynucleotide in another cell, while distinguishable, are each amplified As used herein, "single cell analysis" refers to analysis of genetic information contained in a single cell or cell-like construct distinctly from genetic information contained in other cells or cell-like structures.

DESCRIPTIONS OF PREFERRED EMBODIMENTS

The preferred embodiments are described hereinafter. It is understood that the embodiments are exemplification of the invention, so that the scope of the invention is not limited to such preferred embodiments. It is understood that those skilled in the art can refer to the following preferred embodiments to readily make modifications or changes within the scope of the invention. Any of the embodiments can be appropriately combined by those skilled in the art.

(Method of Amplifying a Polynucleotide in a Cell)

In one aspect, the present invention provides a method of amplifying a polynucleotide in a cell. The amplification method comprises the steps of: encapsulating two or more cells or cell-like structures (including, for example, viruses, organelles (Mt, Nuc), or the like) in liquid droplets, at one cell or construct unit per liquid droplet, by using a sample comprising the cells or cell-like structures; converting the liquid droplets into gel to generate a gel capsule; immersing the gel capsule in one or more types of lysis reagents to lyse the cells or cell-like structures, wherein a polynucleotide in the cells, which has eluted out into the gel capsule, is retained in the gel capsule with a substance binding to the polynucleotide removed; and contacting the polynucleotide with an amplification reagent to amplify the polynucleotide within the gel capsule. The amplification method of the invention can individually amplify a genome or an assembly of genes similar thereto at the so-called single-cell level. The amplification method of the invention materializes individual genome amplification by a very simple and convenient approach. Thus, genome information can be acquired for cells in a unit of 100 cells, unit of 1000 cells, unit of 10000 cells, unit of 100000 cells, or unit or more cells at once. Therefore, this can also be a library.

The step of encapsulation into a liquid droplet in the method of the invention can use any embodiment that is described in detail in the following section (Liquid droplet generation) or other sections.

In one embodiment, any number of cells or cell-like structures greater or equal to 2 can be targeted in the amplification method of the invention, such as 10 or more, 50 or more, 100 or more, 500 or more, 1 thousand or more, 5 thousand or more, 10 thousand or more, 50 thousand or more, 100 thousand or more, 500 thousand or more, 1 million or more, 5 million or more, or 10 million or more. The amplification method of the invention can target a greater number of cells that that used in a conventional single-cell reaction system such as a 0.2 mL or 1.5 mL microtube reaction system.

Anything described in the section of (Cells and cell-like structures) can be used as cells or cell-like structures that can be targeted in the amplification method of the invention. In one preferred embodiment, the method can target cells. In another embodiment, the method can target cell-like structures, particularly viruses, cellular organelles such as mitochondria or nuclei, or the like.

A sample comprising cells or cell-like structures to be provided can be provided in any form in the amplification method of the invention. As the medium contained in a sample (cell or cell-like construct), any medium (including buffer, salt, nutrient, other components, or the like) that is suitable for cells or cell-like structures from the section of (Cells and cell-like structures) can be selected. Any component can be used as such a component, as long as the component is suitable for the generation of liquid droplets. It is preferable that the component is also suitable for conversion into gel. Examples of such a component include, but are not limited to, buffers such as PBS, Tris-HCl, TB, and HEPES, sterilized water, sea water, artificial sea water, various liquid media, and the like. A medium such as surfactant free water or buffer is preferable to generate liquid droplets in some cases.

Any embodiment described in the section of (Liquid droplet preparation) can be used for encapsulating cells or cell-like structures in liquid droplets at one cell or construct unit per liquid droplet. Typically, liquid droplets each encapsulating one cell or cell-like construct can be prepared by using a microchannel and allowing a suspension of cells or cell-like structures to flow in the microchannel and shearing the suspension. Those skilled in the art can perform encapsulation by appropriately adjusting the component or parameter while referring to the description in (Liquid droplet preparation) as well as representative examples provided in the Examples.

Any embodiment described in the section of (Conversion into gel) described below can be used for the step of converting liquid droplets into gel to generate a gel capsule in the amplification method of the invention.

In one embodiment, conversion into gel can be performed by cooling prepared liquid droplets configured so that a liquid droplet or a material of a liquid droplet (e.g., sample comprising cells or cell-like structures) comprises a material of a gel capsule or by applying stimulation with light or the like.

Any material described in the section of (Conversion into gel) described below can be used as the material of a gel capsule.

In the present invention, the step of lysing cells or cell-like structures can be materialized by immersing a gel capsule in one or more types of lysis reagent. Any embodiment described in the section of (Lysis) described below can be used.

In this regard, it is important to process in the step of lysing a cell or cell-like construct so that a polynucleotide in a cell, which has eluted out into the gel capsule, is retained in the gel capsule with a substance binding to the polynucleotide removed.

To maintain a state where a substance binding to a polynucleotide is removed in this manner, it is necessary to ensure that a cell wall/cell membrane structure of cells or cell-like structures is destroyed and denature a protein and substance binding to the polypeptide contained in the cells by adding multiple types of lysis agents in phases or simultaneously. Lysis is achieved by adding a reagent in phases from the destruction of an extracellular layer. Furthermore, the lysate and the lysis reagent remaining in a gel capsule after lysis inhibit polynucleotide amplification in a later stage. Thus, it is desirable in some cases to use a suitable detergent and have the detergent pass through the gel capsule to release the inhibitory substance outside of the gel capsule. To complete these operations within a gel capsule, it is desirable in some cases to have a hydrogel structure that achieves permeation/release of various drug solutions and cell lysates while retaining a polynucleotide within a gel capsule. A residual reagent can be diluted while retaining a genetic material by using a gel capsule. This step can also be repeated. A downstream operation such as an amplification reaction can be performed smoothly by diluting a reagent to a level at which inhibition is not induced.

In the present invention, the step of amplifying a polynucleotide within a gel capsule can be materialized by contacting a polynucleotide with an amplification reagent. Any embodiment specified in in the following (Amplification) can be used.

(Liquid Droplet Generation)

The present invention can encompass encapsulating two or more cells or cell-like structures in liquid droplets by each single cell or a construct unit, at one cell or construct unit per liquid droplet, by using a sample comprising the cells or cell-like structures. In the present invention, a device can comprise a liquid droplet preparation unit for encapsulating cells or cell-like structures in liquid droplets, at one cell or construct unit per liquid droplet.

A liquid droplet can be prepared by using, for example, a microchannel. A liquid droplet preparation unit can comprise a microchannel. Liquid droplets each encapsulating one cell or cell-like construct can be prepared by allowing a suspension of the cells or cell-like structures to flow in a microchannel and shearing the suspension. Shearing can be performed at a certain interval. A suspension can be sheared by using oil. Examples of oil that can be used include mineral oil (e.g., light mineral oil), vegetable oil, silicone oil, and fluorinated oil. Those skilled in the art can prepared lipid droplets so that more than one cell or cell-like construct is not encapsulated per lipid droplet by adjusting the concentration of a suspension, flow rate in the channel, or interval of shearing.

The diameter of liquid droplets is about 1 to 250 μm, more preferably about 10 to 200 μm. For example, the diameter of liquid droplets can be about 1 μm, about 5 μm, about 10 μm, about 15 μm, about 20 μm, about 25 μm, about 30 μm, about 40 μm, about 50 μm, about 80 μm, about 100 μm, about 150 μm, about 200 μm, or about 250 μm.

(Conversion into Gel)

The present invention can encompass a step of converting liquid droplets into gel to generate a gel capsule. In the present invention, a device can comprise a gel capsule generation unit for converting liquid droplets into gel to generate a gel capsule. Liquid droplets can be converted into gel by configuring the liquid droplets to contain a material of a gel capsule and cooling the prepared liquid droplets. Alternatively, liquid droplets can be converted into gel by applying stimulation of a light or the like. Liquid droplets can be configured to contain a material of a gel capsule, for example, by including the material of a gel capsule in a suspension of cells or cell-like structures.

The diameter of a gel capsule can be about 1 to 250 μm, more preferably about 10 to 200 μm, such as about 1 μm, about 5 μm, about 10 μm, about 15 μm, about 20 μm, about 25 μm, about 30 μm, about 40 μm, about 50 μm, about 80 μm, about 100 μm, about 150 μm, about 200 μm, or about 250 μm. The diameter of a gel capsule can be the same as a liquid droplet to be prepared, or the diameter can vary upon conversion into gel.

A material of a gel capsule can comprise agarose, acrylamide, photocurable resin (e.g., PEG-DA), PEG, gelatin, sodium alginate, matrigel, collagen, or the like.

A gel capsule can be a hydrogel capsule. As used herein, "hydrogel" refers to gel whose solvent or dispersion medium retained by a mesh structure of a polymeric substance of colloidal particle is water.

When DNA is extracted in bulk from a large amount of cells, DNA can be purified by phenol/chloroform extraction or ethanol precipitation. However, when intending to acquire/analyze a genetic material from a single cell, the amount of genetic material for each cell is minute, so that the genetic material needs to be individually converted to only a nucleic acid without any loss. An attempt to purify a nucleic acid from a single cell by a general bulk-scale procedure results in extraction of no nucleic acid or only nucleic acid derived from a contaminant. While contamination and loss of target genetic material are significant problems in a single cell experiment, a purified genetic material (e.g., DNA) can be retained in a gel capsule, and the possibility of molecule contamination can be eliminated, by using a gel capsule encapsulating a single cell or cell-like construct. From the operational aspect, a large number of single cells can be processed in parallel with a very simple operation. A step of centrifuging a test tube containing a liquid droplet converted into gel, removing a supernatant, and substituting with a detergent can be performed. Alternatively, a step of filtering a liquid droplet converted into gel with a filter, removing a supernatant, then allowing a detergent to pass therethrough and finally collecting a gel capsule can be performed. A residual reagent can be diluted while retaining a genetic material by using a gel capsule. This step can also be repeated. A downstream operation such as an amplification reaction can be performed smoothly by diluting a reagent to a level where inhibition is not induced.

In one aspect of the invention, a composition comprising a gel capsule or a material thereof can be provided. Such a composition can be useful for amplifying a nucleic acid in a cell at a single-cell level in view of the points described above or below. Such a composition can also be useful for preparing a genome library. In still another embodiment, a composition comprising a gel capsule or a material thereof and a cell in a single-cell state can be provided. Such a composition can be useful for amplifying a nucleic acid in a cell at a single-cell level in view of the points described above or below. Such a composition can also be useful for preparing a genome library. Such a composition can be useful for sequencing a nucleic acid in a cell at a single-cell level.

(Lysis)

The present invention can encompass immersing a gel capsule in one or more lysis reagents to lyse the cells or cell-like structures. In the present invention, a device can comprise a lysis reagent immersion unit for immersing a gel capsule in a lysis reagent. During lysis, a polynucleotide in a cell, which has eluted out into the gel capsule, can be retained in the gel capsule with a substance binding to the polynucleotide removed. Examples of a lysis reagent include enzymes, surfactants, other denaturing agents, reducing agents, and pH modifiers. A combination thereof can also be used. In one aspect of the invention, a composition comprising a lysis reagent for amplifying a nucleic acid in a cell at a single-cell level can be provided.

At least one type of lysis reagent can be selected in some cases from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12. In some cases, at least one type of the lysis reagent is selected from the group consisting of lysozyme, achromopeptidase, protease, sodium dodecyl sulfate, and potassium hydroxide.

If the sole objective is to detect the presence/absence of a part of a sequence in a cell or cell-like construct, aggressive lysis of the cell or cell-like construct is not necessarily required. The presence/absence can be detected based on leakage of nucleic acid from a cell or cell-like construct due to physical stimulation or thermal stimulation. However, it is preferable to aggressively destroy a cell or cell-like construct to isolate a genetic material therein from the cell in a complete state in order to obtain a large amount of information on the entire genome or the like from a single cell. When using a gel capsule, thermal/mechanism stimulation can potentially lead to destruction of a gel capsule, so that it can be preferable to use a lysis reagent in some cases.

When amplifying or analyzing a nucleic acid for each cell for diverse microbes, it is desirable to use a lysis reagent or a combination of lysis reagents that has a certain degree of potency. For example, gram positive bacteria have a cell wall with a thick peptidoglycan layer, so that it is possible that a cell cannot be sufficiently lysed with only a mild lysis reagent.

A potent lysis reagent can potentially inhibit a reaction such as DNA amplification. It is preferable to thoroughly remove such a reagent prior to a reaction downstream. Since a genetic material subjected to analysis or amplification is retained by a gel capsule when a gel capsule is used, a lysis reagent can be removed in a single cell analysis with a small amount of genetic material, so that a potent lysis reagent or a combination of lysis reagents can be used. In addition, use of a potent lysis reagent or a combination of lysis reagents can enable comprehensive nucleic acid amplification or genome analysis regardless of the type of diverse cells (including cells with a cell wall and other types of microbes). A method can comprise a step of removing a lysis reagent and/or contaminant from a gel capsule. A lysis reagent immersion unit also comprises means for removing a lysis reagent and/or contaminant from a gel capsule.

If a target molecule is a part of a nucleic acid or a cell surface marker and the objective is to detect its presence, it can be possible to achieve the objective even with partial or no lysing. If, on the other hand, amplification of the full length of a genomic DNA is intended, the genomic DNA generally has only one molecule in a cell, so that it is necessary to proceed with complete lysis of a cell or cell-like construct and to thoroughly remove binding proteins from the DNA. When the subject is a specimen consisting of hundreds or more species of microbes such as enteric microbes, this makes it possible to lysis all microbes equally and amplify the full genome of all of the microbes. This also makes it possible to prepare a library and ultimately obtain whole-genome sequence information.

(Amplification)

The present invention can comprise contacting a polynucleotide with an amplification reagent to amplify the polynucleotide within the gel capsule. In the present invention, a device can comprise an amplification reagent immersion unit for immersing a gel capsule in an amplification reagent. An amplification reagent immersion unit can optionally comprise means for adjusting the temperature of a gel capsule after immersion in an amplification reagent.

Since a reaction involving heating (80 degrees of higher) can induce re-dissolution of gel (e.g., agarose gel), the shape prepared into an individual particle form is disrupted to nullify single cell isolation in some cases. In such a case, an enzymatic reaction at about 60 degrees or lower is desirable for maintaining the gel liquid droplet shape. A isothermal strand displacement amplification reaction (multiple displacement amplification) is preferable in that the reaction can be performed within such a temperature range and the entire genomic DNA can be amplified. Examples of enzymes used include phi29 polymerase, Bst polymerase, Aac polymerase, and recombinase polymerase.

When performing PCR in order to detect a specific cell (e.g., specific microbe), a specific primer depending on the microbe is generally used. However, when the entire genome is amplified, a random primer is preferably used.

There are thousands to 10s of thousands of types of mRNAs within a cell based on a genomic DNA, and mRNAs individually have a large amount of molecules. For this reason, the objective of expression analysis targeting an RNA would be to find the absolute (relative) amount of expression or type of gene, so that it is possible to quantify how much of what gene is expressed simply by reading out a part of the gene (several dozen bases). When a genomic DNA is targeted, a genomic DNA in principle has only one molecule in one cell so that it can be necessary to increase sequence information of the only one molecule with no omission in order to determine all of the millions of bases thereof. Processing in a gel capsule is advantageous for such amplification. It is advantageous in single-cell analysis to obtain a nucleic acid for sequencing as a whole instead of partial fragmented information from a single cell.

(Cells and Cell-Like Structures)

Examples of cells or cell-like structures in the present invention include, but are not particularly limited to, microbes (e.g., bacteria, fungi, and unicellular animals), cells of a multicellular organism (e.g., somatic cells, germ cells, cultured cells, tumor cells, animal cells, and plant cells), intracellular organs (mitochondria, cell nuclei, and chloroplasts), and viruses.

For cells of an organism with a known genome sequence, measurement of RNA can be intended to find which gene therein is expressed. For analyzing an organism with unknown genome sequence and/or genetic information, information on the genome itself needs to be obtained prior to RNA analysis. In such a case, amplification of a genome sequence at a single-cell level by the method of the invention using a gel capsule is advantageous.

The present invention can use a sample comprising two or more cells or cell-like structures. Two or more cells can be derived from a plurality of organisms. Examples of samples include microbial samples, tissue samples, mixed samples of a symbiotic microbe and a host organism, and a sample comprising a microbe and cell retrieved from an animal/human specimen. Examples of microbial samples include bacterial flora samples as well as samples containing two or less species of cells or cell-like structures and samples containing cells or cell-like structures other than bacteria such as fungi. Examples of samples comprising a microbe and cell retrieved from a human specimen include stool, saliva, sputum, surgical detergent, blood, and swab of skin/mucus membrane of the body. While a sample can be used directly, a sample can be used after an operation to separate a cell or microbe.

Examples of microbes that can be the subject in the present invention include, but are not limited to, eubacteria, *E. coli, Bacillus subtilis*, cyanobacteria, cocci, *Bacillus*, Spirillum, gram negative bacteria, gram positive bacteria, archaea, fungi, and the like. Examples of bacteria that can be the subject in the present invention include bacteria such as Negibacteria, Eobacteria, Deinococci, Deinococci, Deinococcales, Thermales, Chloroflexi, Anaerolineae, Anaerolineales, Caldilineae, Chloroflexales, Herpetosiphonales, Thermomicrobia, Thermomicrobiales, Sphaerobacterales, Ktedonobacteria, Ktedonobacterales, Thermogemmatisporales, Glycobacteria, Cyanobacteria, Gloeobacterophvceae, Gloeobacterales, Nostocophyceae, Synechococcophvcidae, Synechococcales, Nostocophycidae, Chroococcales, Oscillatoriales, Nostocales, Pseudanabaenales, Spirochaetes, Spirochaetes, Spirochaetales, Fibrobacteres, Fibrobacteria, Gemmatimonadetes, Gemmatimonadetes, Gemmatimonadales, Chlorobi, Chlorobea, Chlorobiales, Ignavibacteria, Ignavibacteriales, Bacteroidetes, Bacteroidia, Bacteroidales, Flavobacteriia, Flavobacteriales, Sphingobacteriia, Sphingobacteriales, Cytophagia, Cytophagales, Planctomycetes, Planctomycea, Planctomycetales, Phycisphaerae, Phycisphaerales, Chlamydiae, Chlamydiae, Chlamydiales, Verrucomicrobia, Verrucomicrobiae, Verrucomicrobiales, Opitutae, Opitutales, Puniceicoccales, Spartobacteria, Chthoniobacterales, Lentisphaerae, Lentisphaeria, Lentisphaerales, Victivallales, Proteobacteria, Alphaproteobacteria, Rhodospirillales, Rickettsiales, Rhodobacterales, Sphingomonadales, Caulobacterales, Rhizobiales, Parvularculales, Kordiimonadales, Sneathiellales, Kiloniellales, Betaproteobacteria, Burkholderiales, Hydrogenophilales, Methylophilales, Neisseriales, Nitrosomonadales, Rhodocyclales, Procabacteriales, Gammaproteobacteria, Chromatiales, Acidithiobacillales, Xanthomonadales, Cardiobacteriales, Thiotrichales, Legionellales, Methylococcales, Oceanospirillales, Pseudomonadales, Alteromonadales, Vibrionales, Aeromonadales, Enterobacteriales, Pasteurellales, Deltaproteobacteria, Desulfurellales, Desulfovibrionales, Desulfobacterales, Desulfarculales, Desulfuromonadales, Syntrophobacterales, Bdellovibrionales, Myxococcales, Epsilonproteobacteria, Campylobacteria, Nautiliales, Acidobacteria, Acidobacteria, Acidobacteriales, Holophagae, Holophagales, Acanthopleuribacterales, Aquificae, Aquificae, Aquificales, Deferribacteres, Deferribacteres, Geovibriales, Thermodesulfobacteria, Thermodesulfobacteria, Thermodesulfobacteriales, Nitrospirae, Nitrospira, Nitrospirales, Fusobacteria, Fusobacteriia, Fusobacteriales, Synergistetes, Synergistia, Synergistales, Caldiserica, Caldisericia, Caldisericales, Elusimicrobia, Elusimicrobia, Elusimicrobiales, Armatimonadetes, Armatimonadia, Armatimonadales, Chthonomonadetes, Chthonomonadales, Fimbriimonadia, Fimbriimonadales, Posibacteria, Thermotogae, Thermotogae, Thermotagales, Firmicutes, Bacilli, Bacillales, Lactobacillales, Clostridia, Clostridiales, Halanaerobiales, Thermoanaerobacterales, Natranaerobiales, Negativicutes, Selenomonadales, Erysipelotrichia, Erysipelotrichales, Thermolithobacteria, Thermolithobacterales, Tenericutes, Mollicutes, Mycoplasmatales, Entomoplasmatales, Acholeplasmatales, Anaeroplasmatales, Actinobacteria, Actinobacteria, Actinomycetales, Actinopolysporales, Bifidobacteriales, Catenulisporales, Corynebacteriales, Frankiales, Glycomycetales, Jiangellales, Kineosporiales, Micrococcales, Micromonosporales, Propionibacteriales, Pseudonocardiales, Streptomycetales, Streptosporangiales, Dictyoglomi, Dictyoglomia, Dictyoglomales, Chrysiogenetes, Chrysiogenetes, Chrysiogenales, and Haloplasmatales. Comprehensive analysis for each cell can also be performed on a sample containing a plurality of bacteria thereamong.

(Composition/Kit)

In one aspect of the invention, a composition or a kit that can be used in the method of the invention is provided. In the present invention, a composition for amplifying a nucleic acid in a cell at a single-cell level can be provided. A composition can comprise a gel capsule or a material thereof. Use of a gel capsule can be advantageous for amplifying a nucleic acid in a cell at a single-cell level as described elsewhere herein. In the present invention, a composition for preparing a genome library can be provided. Use of a gel capsule can be advantageous for preparing a library as described elsewhere herein.

In the present invention, a composition for amplifying a nucleic acid in a cell at a single-cell level, comprising gel capsule or a material thereof, and a cell in a single cell state can be provided. A composition can be subjected to a step in a method described elsewhere herein for use in nucleic acid amplification at a single-cell level. In the present invention, a composition for preparing a genome library, comprising a gel capsule or a material thereof, and a cell in a single cell state can be provided. A composition can be subjected to a step in a method described elsewhere herein for use in preparation of a genome library. In the present invention, a composition for sequencing a nucleic acid in a cell at a single-cell level, comprising a gel capsule or a material thereof, and a cell in a single cell state can be provided. A composition can be subjected to a step in a method described elsewhere herein for use in sequencing of a nucleic acid in a cell at a single-cell level.

In one aspect of the invention, a composition for amplifying a nucleic acid in a cell at a single-cell level, comprising a lysis reagent, is provided. A lysis reagent can comprise at least one selected from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12.

A kit for amplifying a nucleic acid in a cell at a single-cell level can be provided. A kit can comprise, for example, a material of a gel capsule and optionally one or more reagents. Examples of the one or more reagents include a lysis reagent.

(Method of Preparing a Genome Library and Device for Preparing a Genome Library)

The present invention can provide a method of purifying a polynucleotide from diverse microbes within a gel capsule and preparing a genome library from the amplified polynucleotide within the gel capsule. In one aspect of the invention, a method and device for preparing a genome library for lysing a cell and amplifying a genome with a simple operation can be provided.

When a genome is analyzed from a single cell of microbe, an operation for transferring each cell into a reaction vessel is required for performing a genome amplification reaction for each cell. It is difficult to subject a small non-organism particle and a microbe to a reaction separately in conventional cell isolating technology, i.e., flow cytometry, where the amount of reaction solution in the vessel is excessively large at several billion-fold or more of the microbe volume in microliters. For this reason, a reaction frequently resulted in contamination or amplification error, such that the yield of pure amplified nucleic acid samples from a single cell was low.

The maximum capacity for parallel processing was limited as several hundred reactions, so that comprehensive analysis of genome DNA at a unit of one cell from thousands or more species of microbes in the environment was challenging. Solving the problem requires a method of creating a large number of reaction environments at a scale matching a single microbe, sequentially performing cell lysing and enzymatic reaction therein, purifying and then amplifying a minute amount of genomic DNA in parallel, and procuring an amplified nucleic acid sample in a form that can be stored and reanalyzed.

WO 2017/218486 describes performing single cell analysis by using a microchannel and preparing gel beads. However, WO 2017/218486 does not specify the detailed conditions and the like that are compatible with microbial samples.

Japanese National Phase PCT Laid-open Publication No. 2017-532024 describes a method and device for preparing, through isolating, lysing, and barcoding, nucleic acids from individual cells in a high-throughput manner. However, the method and device described in Japanese National Phase PCT Laid-open Publication No. 2017-532024 targets mRNAs, not genomic DNAs. The method and device also cannot be applied to microbial samples with a hard cell wall.

Single-cell genome sequencing at ultra high-throughput with microfluidic droplet barcoding Nat Biotechnol. 2017 July; 35(7): 640-646 describes that a microchannel is used to prepare gel beads and analyze the genome of a single microbial cell. Since the method described therein digests a microbial sample with an enzymatic solution and then adds a barcode sequence to the genomic DNA, DNA is not amplified inside the gel. Since DNA is not amplified, reanalysis is impossible so that a sample of interest cannot be evaluated in detail. Further, the genome completeness is only 0.1% or less.

Virtual microfluidics for digital quantification and single-cell sequencing Nature Methods volume 13, pages 759-762 (2016) describes that the entire solvent to which enteric microbes are dispersed is converted into gel, the microbes are lysed in the gel, and then the genome is amplified. The document also describes that a genome amplification spot labeled with a fluorescent dye was punched out with a needle and retrieved, and genome amplification was performed again to determine the whole genome. However, since the size of the gel described therein is large, bacteriolysis and DNA amplification reaction are insufficient, such that the genome completeness is low at an average of 10%.

Massively parallel whole genome amplification for single-cell sequencing using droplet micro fluidics describes a method of amplifying a genome of a single cell of a microbe using a special microchannel for encapsulating a microbial cell in a liquid droplet with a bacteriolysis solution and then fusing the liquid droplet with a second liquid droplet comprising a whole genome amplification reagent. Since gel beads are not formed with the genome amplification method in said document, the method is applicable only under a weak bacteriolysis condition and is applicable only to some microbes. Since conversion into gel is not performed, separation and collection for preparing a library are not easy.

The method of preparing a genome library of the invention in some cases have the steps of: encapsulating cells of one or more microbes in liquid droplets, at one cell per liquid droplet, using a sample comprising the microbes; converting the liquid droplets to generate a gel capsule; immersing the gel capsule in one or more types of lysis reagents to lyse the cells and retaining a polynucleotide, which has eluted out into the gel capsule, within the gel capsule; immersing the gel capsule in an amplification regent to amplify the polynucleotide within the gel capsule; and sorting, separating, and collecting each gel capsule with the amplified polynucleotide.

In some cases, the method of preparing a genome library of the invention prepares the liquid droplet encapsulating the cell by allowing a suspension of the cell to flow in a microchannel and shearing the suspension. In some cases, a diameter of the liquid droplets is 1 to 250 μm in the method of preparing a genome library of the invention. In some cases, a diameter of the gel capsule is 1 to 250 μm in the method of preparing a genome library of the invention. In some cases, the gel capsule is formed from agarose, acrylamide, photocurable resin, PEG, gelatin, sodium alginate, matrigel, or collagen in the method of preparing a genome library of the invention. In some cases, the gel capsule is a hydrogel capsule in the method of preparing a genome library of the invention.

In some cases, the method of preparing a genome library of the invention has the step of removing the lysis reagent and contaminant from the gel capsule after immersing the gel capsule in the lysis reagent.

In some cases, at least one type of the lysis reagent is selected from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12 in the method of preparing a genome library of the invention.

In some cases, the method of preparing a genome library of the invention is a method of manipulating a cell for library formation and whole genome analysis of a genome of a single cell derived from an uncultured microbe.

In some cases, the device for preparing a genome library of the invention comprises: a liquid droplet preparation unit for encapsulating cells in liquid droplet, at one cell per liquid droplet; a gel capsule generation unit for converting the liquid droplets into gel to generate a gel capsule; a lysis reagent immersion unit for immersing the gel capsule in a lysis reagent; a removal unit for removing a contaminant from the gel capsule; an amplification reagent immersion unit for immersing the gel capsule in an amplification reagent; and a sorting unit for sorting the gel capsule and housing the gel capsule in a housing container.

The present invention can provide a method and device for preparing a genome library for cell lysing and genome amplification by a simple operation.

Examples of embodiments of a method and device for preparing a genome library include the following embodiments.

(Embodiment 1) A method of preparing a genome library having the steps of:

encapsulating cells of one or more microbes in liquid droplets, at one cell per liquid droplet, by using a sample comprising the microbes;

converting the liquid droplets into gel to generate a gel capsule;

immersing the gel capsule in one or more types of lysis reagents to lyse the cells and retaining a polynucleotide, which has eluted out into the gel capsule, within the gel capsule;

immersing the gel capsule in an amplification regent to amplify the polynucleotide within the gel capsule; and sorting, separating, and collecting each gel capsule with the amplified polynucleotide.

(Embodiment 2) The method of preparing a genome library of embodiment 1, having the step of removing the lysis reagent and contaminant from the gel capsule after immersing the gel capsule in the lysis reagent.

(Embodiment 3) The method of preparing a genome library of embodiment 1 or 2, wherein the liquid droplets are prepared by allowing a suspension of the cells to flow in a microchannel and shearing the suspension with oil.

(Embodiment 4) The method of preparing a genome library of embodiment 3, wherein a diameter of the liquid droplets is 1 to 250 μm.

(Embodiment 5) The method of preparing a genome library of any one of embodiments 1 to 4, wherein a diameter of the gel capsule is 1 to 250 μm.

(Embodiment 6) The method of preparing a genome library of any one of embodiments 1 to 5, wherein the gel capsule is formed from agarose, acrylamide, photocurable resin, PEG, gelatin, sodium alginate, matrigel, or collagen.

(Embodiment 7) The method of preparing a genome library of any one of embodiments 1 to 6, wherein at least one type of the lysis reagent is selected from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12.

(Embodiment 8) The method of preparing a genome library of any one of embodiments 1 to 7, wherein the gel capsule is a hydrogel capsule.

(Embodiment 9) The method of preparing a genome library of any one of embodiments 1 to 8, wherein the method of preparing a genome library is a method of manipulating a cell for library formation and whole genome analysis of a genome of a single cell derived from an uncultured microbe.

(Embodiment 10) A device for preparing a genome library, comprising:

a liquid droplet preparation unit for encapsulating cells in liquid droplets, at one cell per liquid droplet;

a gel capsule generation unit for converting the liquid droplets into gel to generate a gel capsule;

a lysis reagent immersion unit for immersing the gel capsule in a lysis reagent;

a removal unit for removing a contaminant from the gel capsule;

an amplification reagent immersion unit for immersing the gel capsule in an amplification reagent; and a sorting unit for sorting the gel capsule and housing the gel capsule in a housing container.

(Data/Database/Data Processing)

A subject of data acquisition or analysis can be selected from a cluster of a large number of cells or cell-like structures and a cluster of gel capsules or genome libraries derived from the cells or cell-like structures. For example, the present invention can generate a subpopulation comprising cells or cell-like structures by a method comprising the step of generating a subpopulation comprising at least one cell or cell-like construct based on a nucleic acid sequence of two or more cells or cell-like structures from a cluster comprising the cells or cell-like structures. Generation of a subpopulation can reduce the effort for the step of sequencing or creating a genome draft based on a sequencing read.

In one embodiment of the disclosure, two or more cells or cell-like structures provided separately can be sorted based on nucleic acid information derived from the cells or cell-like structures. The sorted cells or cell-like structures can be optionally analyzed. For sorting, several sorting can be performed, such as sequencing from PCR and determining a partial sequence, checking the presence/absence of a specific genetic sequence, and referencing the DNA yield.

In one embodiment of the disclosure, nucleic acid information derived from two or more cells or cell-like structures can be sorted after sequencing. Nucleic acid information derived from two or more cells or cell-like structures can be provided as an aggregate of nucleic acid information for each of the cells or cell-like structures and then the nucleic acid information can be sorted for each of the cells or cell-like structures based on all or part of the nucleic acid information. Sorted nucleic acid information can be optionally analyzed.

In one embodiment of the disclosure, the obtained sequence information can be recorded as a database. A database can be recorded on an automatic data constructing/ providing system. A database can store each piece of sequence information derived from a single cell or cell-like construct separately. Each piece of sequence information can be categorized and organized. Desirable categorization is categorization by each organism species. A categorized cluster does not have contamination from sequence information for other species or organisms, so that complete sequence information within a cluster can be constructed based thereon. When constructing complete sequence information, information can be re-categorized. Information obtained by analysis can also be used for fine-tuning categorization of newly-obtained sequence information derived from a single cell or cell-like construct.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. While the present invention is described hereinafter based on the Examples, the above descriptions and the following Examples are provided for the sole purpose of exemplification, not limitation of the present invention. Thus, the scope of the present invention is not limited to the embodiments and Examples that are specifically described herein and is limited only by the scope of claims.

EXAMPLES

The Examples of the invention are described hereinafter while referring to the appended FIGS. 1 to 7. The Examples described hereinafter do not limit the invention recited in the claims. Further, not all of the configurations described hereinafter are necessarily indispensable for the present invention.

1. Preparation of a Single Cell Amplified Genome Library Derived from Mouse Enteric Microbes A single cell amplified genome library 17 was prepared from mouse enteric microbes harvested from a mouse stool sample. This Example prepares the genome library 17 by harvesting and amplifying a genomic DNA 14, but a messenger RNA or other polynucleotides can be collected and amplified to prepare a polynucleotide library thereof. A sample can be either a sample comprising only the same species of microbes or a sample comprising different species of microbes. A sample only needs to comprise at least one microbe.

In the experiment, a stool of a male ICR mouse (66-weeks old) (Tokyo Laboratory Animals Science) was collected in a tube with a volume of 1.5 mL (1212-10 SSIbio) (not shown) and ground down until there was no more solid matter using a homogenizer (ASPES-50, AS ONE) in 500 μL of phosphate buffered saline (PBS) (Dulbecco's Phosphate-Buffered Saline, 14190-144, Thermo Fisher Scientific). After repeating the operation of centrifuging the sample for 2 seconds at 2000×g (himac CF15RX, Koki Holdings) and retrieving the supernatant twice, the sample was centrifuged for 3 minutes at 15000×g to harvest mouse enteric microbes.

A cell suspension of mouse enteric microbes was obtained by centrifugally washing the bacterial cell pellets with PBS twice and suspending the pellets in PBS. The cell concentration in the prepared cell suspension was measured (microscope; CKX41 OLYMPUS, bacteria calculation board, A161, 2-5679-01, AS ONE) and an ultra-low melting point agarose (A5030-10G, SIGMA-ALDRICH) was added so that the final concentration would be 1.5% to prepare an enteric microbial suspension 1 used for the preparation of a gel capsule 11 (final cell concentration: $1.5 \times 10^3$ cells/μL)

A liquid microdroplet 3 was prepared and a single cell 4 of the mouse enteric microbes was encapsulated within the liquid microdroplet 3 by using a microchannel 2 that was self-made using polydimethylsiloxane (Sylgard 184: Dow Corning). As shown in FIG. 1, this Example used the microchannel 2 consisting of a first channel 5, second channel 6, third channel 7, and fourth channel 8, wherein adjacent channels are arranged perpendicularly, but a microchannel 2 with such channels connected in a roughly T shape can also be used. This Example used a microchannel 2 with a width of 34 μm and a height of 50 μm, but the size of the microchannel 2 can be appropriately changed depending on the size of the liquid microdroplet 3 to be prepared or the size of the single cell 4 to be encapsulated.

A liquid microdroplet 3 with a diameter of 50 μm was prepared by introducing the enteric microbial suspension 1 from the first channel 5 (aqueous phase inlet) and introducing Pico-Surf1 (2% in Novec 7500) (Sphere Fluidics) from the second channel 6 and the fourth channel 8 (oil phase inlets) (hereinafter, referred to as "oil 10") to shear the enteric microbial suspension 1, and the liquid microdroplet 3 was allowed to flow in the third channel 7 and collected in a 0.2 mL tube 9. About 450 thousand liquid microdroplets 3 were prepared at a rate of 500 liquid droplets/second. The cell concentration within the liquid microdroplet 3 was 0.1 cells/droplet.

This Example facilitates encapsulation of a single cell 4 per liquid microdroplet 3 by using a uniform diameter of liquid microdroplets 3 of 50 μm. Considering the size of the single cell 4, the diameter of the liquid microdroplet 3 is, for example, 1 to 250 μm and preferably 20 to 200 μm.

Figure 2:
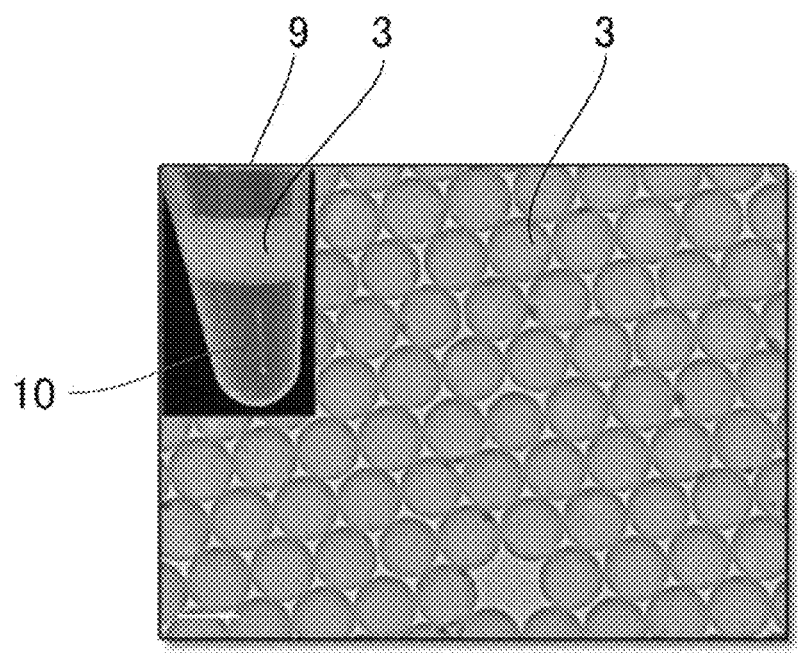
FIG. 2 is a diagram showing a liquid microdroplet housed in a tube of Example 1 of the invention.

As shown in FIG. 2, a plurality of liquid microdroplets 3 and oil 10 are contained in the tube 9, but the liquid microdroplets 3 aggregate in the top layer due to a lower specific gravity than that of the oil 10.

The tube 9 was then cooled for 15 minutes on ice, and the liquid microdroplets 3 were converted into gel with ultra-low melting point agarose. The liquid microdroplet 3 converted into gel is the gel capsule 11. Since the diameter of the liquid microdroplet 3 is 50 μm, the diameter of the gel capsule 11 would also be 50 μm. The diameter of the gel capsule 11 is, for example, 1 to 250 μm, and preferably 20 to 200 μm. The permeation rate of a bacteriolysis reagent 13 described below into each of the gel capsules 11 can be more uniform by preparing the gel capsules 11 to have a uniform diameter.

Figure 3:
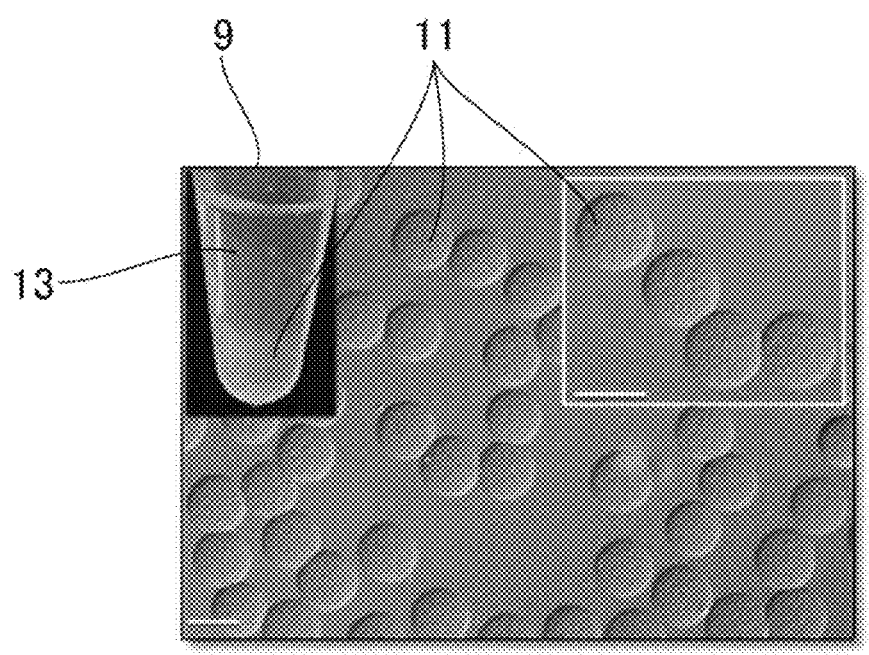
FIG. 3 is a diagram showing a gel capsule housed in a tube of Example 1 of the invention.
Figure 4:
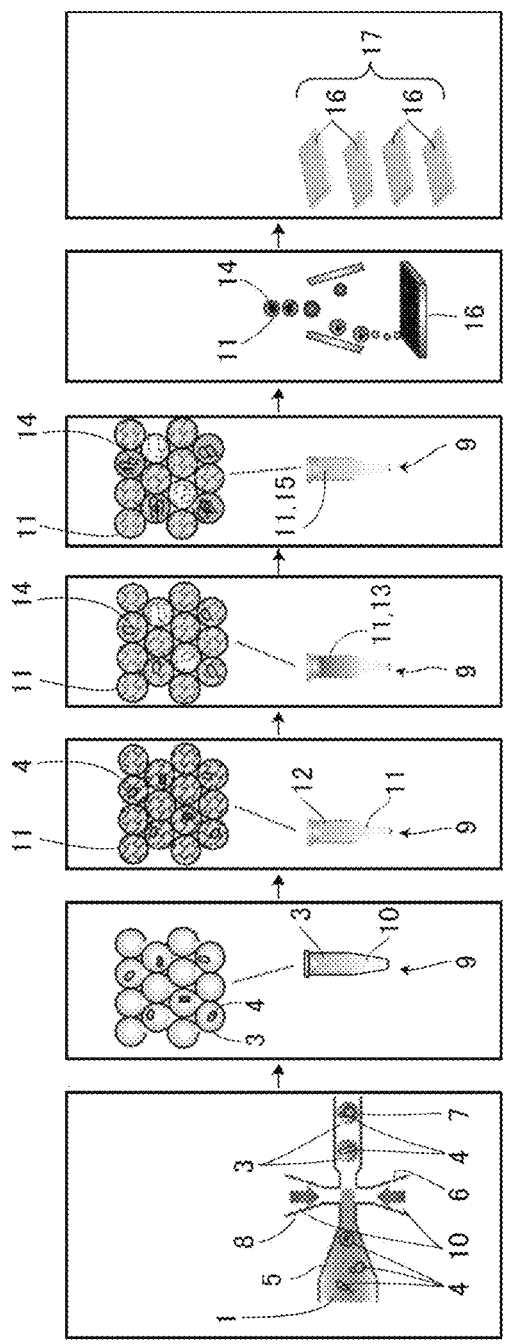
FIG. 4 is a diagram showing the steps of preparing a single cell amplified genome library of Example 1 of the invention.

20 μL of 1H,1H,2H,2H-perfluoro-1-octanol (SIGMA-ALDRICH) was then added to the tube 9 and the oil 10 in the bottom layer was removed. Acetone (FUJIFILM Wako Pure Chemical) (500 μL) and isopropanol (500 μL) (FUJIFILM Wako Pure Chemical) were then added in order and the tube was centrifugally washed to remove the oil 10. Centrifugal washing for removing the oil 10 was performed by a removal unit 25 described below. This Example assumes that the oil 10 permeated into the gel capsule 11 is included as contaminants. The tube was further added with 500 μL of PBS and centrifugally washed three times so that the gel capsule 11 was suspended in an aqueous layer (PBS) 12. As shown in FIG. 3, the gel capsule 11 aggregates in the bottom layer because its specific gravity is higher than that of the aqueous layer 12.

Subsequently, the gel capsules 11 were sequentially immersed in the bacteriolysis reagent 13 used as a lysis reagent. The portions other than the portions of interest for collection such as the cell wall of the cell 4 inside the gel capsule 11 were lysed to let the genomic DNA 14 elute out into the gel capsule 11.

Specifically, lysozyme (10 U/μL) (R1804M, Epicentre), which is one type of bacteriolysis reagent 13, was added to the tube 9 to lyse the cell 4. Achromopeptidase (850 U/mL) (015-09951, FUJIFILM Wako Pure Chemical), which is one type of bacteriolysis reagent 13, was then added to the tube 9. Protease K (1 mg/mL) (MC5005, Promega) and 0.5% sodium dodecyl sulfate (SDS) (71736-100ML, SIGMA-ALDRICH), which are types of bacteriolysis reagent 13, were then added to the tube 9 to lyse the cell 4. The tube was then centrifugally washed 5 times, and components other than the genomic DNA 14 of the lysed cell 4 (contaminants) were removed from the tube 9. Subsequently, the gel capsule 11 was immersed in Buffer D2 (QIAGEN), an aqueous solution comprising potassium hydroxide, which is a type of bacteriolysis reagent 13, for lysing of residual components and denaturation of the genomic DNA 14. As described above, the bacteriolysis regents 13 used in this Example are lysozyme, achromopeptidase, protease K, sodium dodecyl sulfate, and Buffer D2. While potassium hydroxide is also used in a normal DNA amplification reaction step, it is also considered as one of the bacteriolysis reagents 13 in this Example because potassium hydroxide also has an effect of bacteriolysis. Since the gel capsule 11 is immersed in the bacteriolysis reagent 13 for a short period of time, the eluted genomic DNA 14 would not flow out of the gel capsule 11 due to the bacteriolysis regent 13, but is retained within the gel capsule 11. This Example assumes that the bacteriolysis reagent 13 permeated into the gel capsule 11 is also included as contaminants.

This example can attain a sufficient cleaning effect by sequentially adding lysozyme, achromopeptidase, and protease K and adding sodium dodecyl sulfate to lyse the cell 4, and then centrifugally washing only before adding Buffer D2. However, centrifugal washing can be performed after lysing the cell 4 with each bacteriolysis reagent 13.

In this manner, the genomic DNA 14 of interest can be harvested by lysing the cell 4 with a plurality of types of bacteriolysis reagents 13. By centrifugal washing after immersion in the bacteriolysis reagent 13, contaminants such as the bacteriolysis reagents 13 and components other than the polynucleotide of the lysed cell 4 can be removed and the genomic DNA 14 can be purified without inhibiting a subsequent genomic DNA amplification reaction.

An amplification reagent 15 was added to the tube 9 comprising the gel capsule 11 retaining the genomic DNA 14 denatured in a potassium hydroxide solution (Buffer D2), and the gel capsule 11 was immersed in the amplification reagent 15. Specifically, MDA (Multiple Displacement Amplification) using strand displacing DNA synthase phi29 DNA polymerase was used. In this regard, the gel capsule was immersed in a whole genome amplification reaction reagent REPLI-g Single Cell Kit (QIAGEN) to perform 3 hours of whole genome amplification reaction (S1000 thermal cycler, Bio-Rad). The amplification reagent 15 (REPLI-g Single Cell Kit) contains a component that neutralizes a potassium hydroxide solution (Buffer D2).

Figure 5:
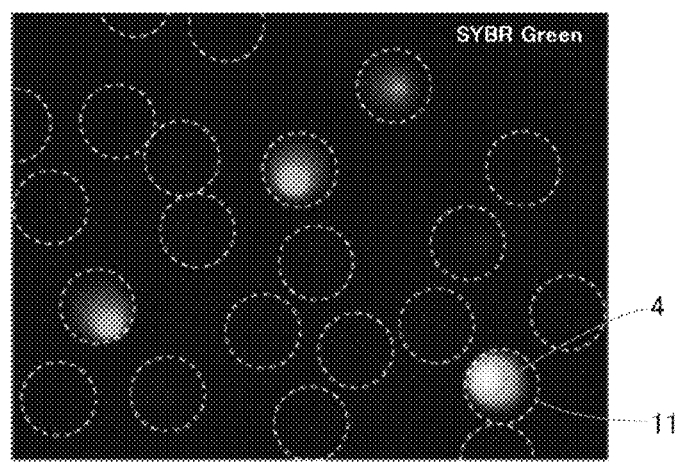
FIG. 5 is a diagram showing a genomic DNA within a gel capsule stained with SYBR green of Example 1 of the invention.

After centrifugally washing the gel capsule 11 after the whole genome amplification using Tris-EDTA, the sample was stained with a fluorescent DNA intercalator with a staining reagent SYBR green (S7563, Thermo Fisher Scientific) as shown in FIG. 5. Other known staining reagents such as Evagreen (31000, Como Bio Co., Ltd.) can also be used for staining.

The gel capsules 11 retaining the genomic DNA 14 amplified to a predetermined extent or more by a flow cytometer 30 (BD FACSMelody cell sorter, BD Biosciences) were sorted, and individually collected in a plate 16 (PCR-96-FS-C, Axygen) used as a housing container, to which 1 μL of PBS was added in advance. The gel capsules 11 can also be sorted by dropping the gel capsule 11 on a slide glass and individually harvesting the gel capsules 11 exhibiting fluorescence under an observation with a microscope by using a micropipette (e.g., Microdispenser, Drummond Scientific, or the like).

After lysing the gel capsules 11 by heating (S1000 thermocycler, Bio-Rad) individually collected gel capsules 11 at 65 degrees, secondary amplification by MDA was performed within wells of each plate 16. A mouse enteric microbe derived single cell amplified genomic library 17 can be prepared by accumulating a large number of the plates 16 housing the gel capsules 11.

A population of the gel capsules 11 prior to the secondary amplification was refrigerated at 4° C. in Tris-EDTA. The single cell amplified genome library 17 can be stored for an extended period by freezing at −20° C. or −80° C. until use in a subsequent experiment.

Figure 6:
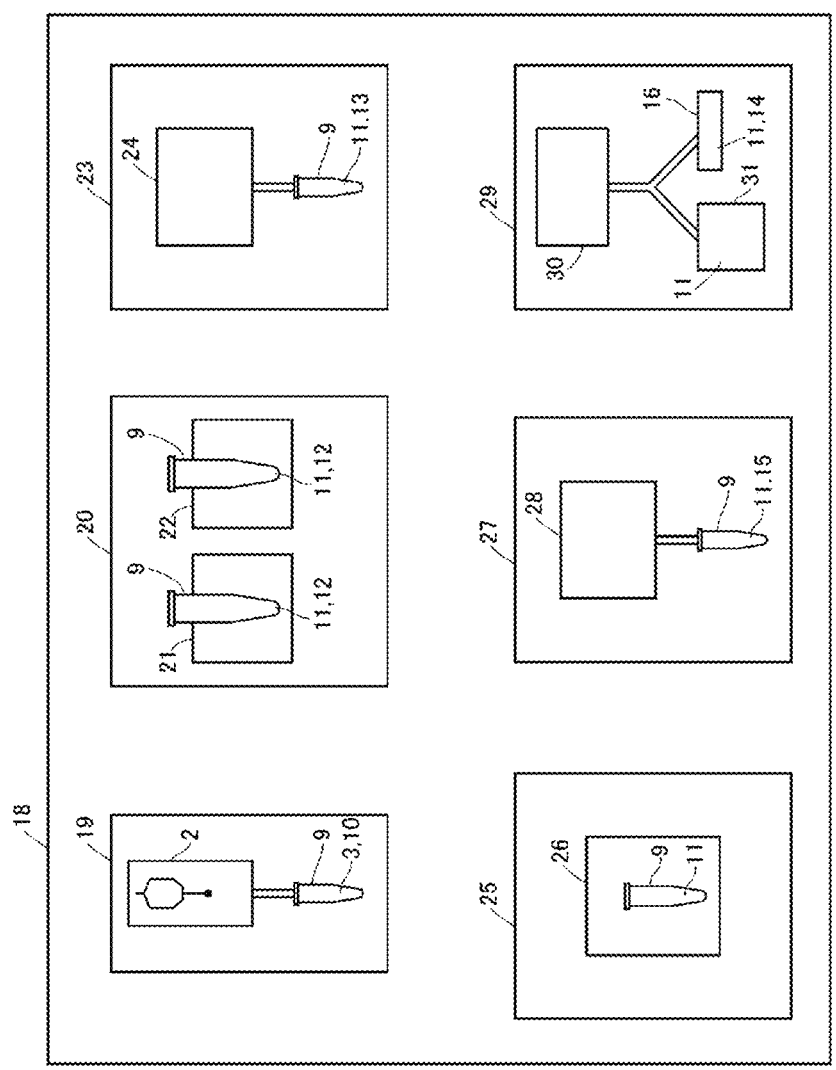
FIG. 6 is a schematic diagram showing a genome library preparation device of Example 1 of the invention.
Figure 7:
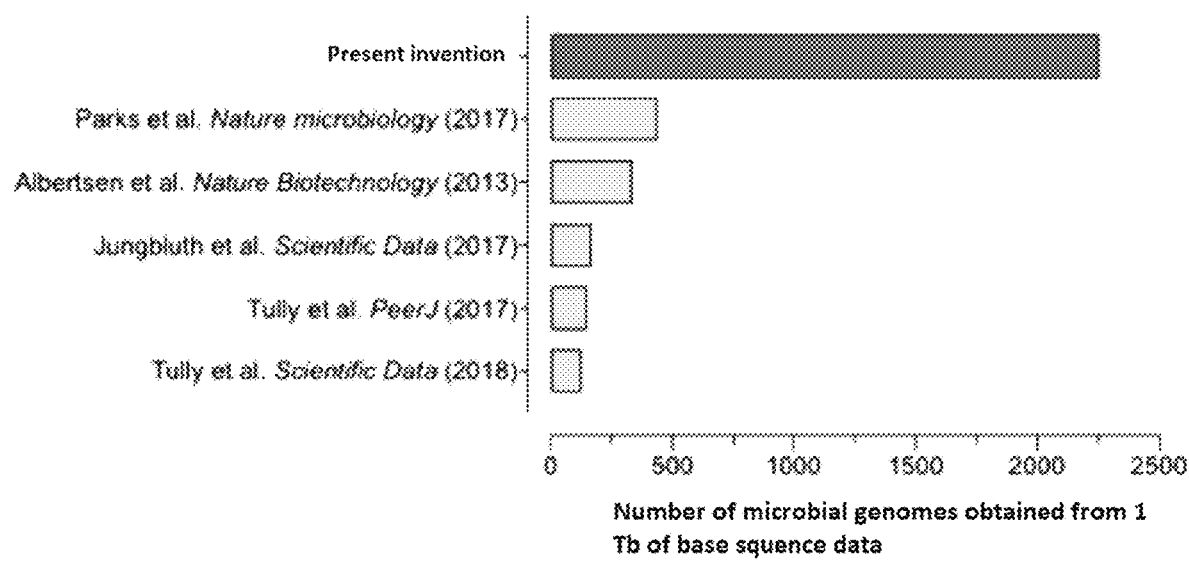
FIG. 7 is a diagram comparing the number of microbial genomes obtained from 1 Tb of base sequence data of Example 1 of the invention.

A preparation device 18 of the single cell amplified genome library 17 is now described by referring to FIG. 6. The preparation device 18 comprises a liquid droplet preparation unit 19 for encapsulating the single cell 4 within the liquid microdroplet 3 with the microchannel 2. The generated liquid microdroplet 3 is housed in the tube 9.

The preparation device 18 comprises a gel capsule generation unit 20 for converting the liquid microdroplet 3 into gel to generate the gel capsule 11. The gel capsule generation unit 20 has a cooling unit 21, so that the liquid microdroplet 3 can be cooled while being housed in the tube 9. The gel capsule generation unit 20 also has a UV ray irradiation unit 22 for irradiating UV rays while the liquid microdroplet 3 is housed in the tube 9, so that the gel capsule 11 can be generated using a photocurable resin. The gel capsule generation unit 20 can also have only one of the cooling unit 21 or the UV ray irradiation unit 22.

The preparation device 18 also comprises a lysis reagent immersion unit 23 for infusing the bacteriolysis reagent 13 into the tube 9 housing the gel capsule 11 to immerse the gel capsule 11 in the bacteriolysis reagent 13. The bacteriolysis reagent 13 is infused into the tube 9 from a lysis reagent infusion unit 24.

The preparation device 18 comprises the removal unit 25 for removing contaminants including the oil 10 and bacteriolysis reagent 13 from the gel capsule 11. The removal unit 25 has a centrifugal washing unit 26. After immersing the gel capsule 11 in the bacteriolysis reagent 13 for a predetermined time, the bacteriolysis reagent 13 and contaminants are removed from the gel capsule 11 and the tube 9 with the centrifugal washing unit 26.

The preparation device 18 also comprises an amplification reagent immersion unit 27 for immersing the genomic DNA 14 retained in the gel capsule 11 in the amplification reagent 15 for amplifying the genomic DNA 14. The amplification regent 15 is infused into the tube 9 from an amplification reagent infusion unit 28.

The preparation device 18 also comprises a sorting unit 29 for sorting the gel capsule 11 retaining the genome DNA 14 amplified to a predetermined level or higher. The sorting unit 29 has a flow cytometer 30. The gel capsule 11 retaining the genome DNA 14 amplified to a predetermined level or higher is sorted and collected in the plate 16. The gel capsule 11 that does not retain the genome DNA 14 amplified to a predetermined level or higher is collected in another container 31.

2. Whole Genome Sequencing from a Single Cell Amplified Genome Library

The whole genome was determined and analyzed from the single cell amplified genome library 17. Specifically, PCR was performed on the V3V4 region of a 16S rRNA gene by using a part of each amplified genome in the single cell amplified genome library 17 (6.25 μL PrimeSTAR Max DNA Polymerase (R045B, Takara Bio), 0.5 μL 10 μM Primer Forward (5'-TCGTCGGCAGCGTCA-GATGTGTATAAGAGACAGCCTACGGG-NGGCWGCAG-3' (SEQ ID NO: 1)), 0.5 μL 10 μM Primer Reverse (5'-GTCTCGTGGGCTCG-GAGATGTGTATAAGAGACAGGAC-TACHVGGGTATCTAATCC-3' (SEQ ID NO: 2)), 1.0 μL DNA diluent, 4.25 μL UltraPure DNase/RNase-Free Distilled Water (10977-015, Thermo Fisher Scientific) (S1000 thermocycler, Bio-Rad). The PCR reaction conditions were initial thermal denaturation at 95° C. for 5 minutes, thermal denaturation at 98° C. for 10 seconds, annealing at 51° C. for 15 seconds, and elongation reaction at 72° C. for 5 seconds. After 27 cycles thereof and a reaction at 72° C. for 5 minutes, the product was stored at 4° C. After checking the presence/absence of a PCR product by agarose electrophoresis (electrophoresis tank: Mupid-exU, EXU-1, Mupid, marker: GeneRuler™ 1 kb DNA Ladder, #SM0318, Fermentas, stain: Midori Green Direct, NE-MG06, Nippon Genetics, loading buffer: 6× Loading Buffer, 9157, Takara Bic) (electrophoretic condition: 100V, 15 min), a sequence was analyzed for samples observed to be amplified using the Sanger method (DNA sequencing outsourcing service by FASMAC). A library was prepared with Nextera XT DNA sample prep kit (Illumina, FC-131-1096) for samples for which a PCR product was obtained. 2×75 bp of pair-end reads (3.99 Gb) were obtained by whole genome sequencing using Miseq (Illumina, SY-410-1003). After assembling sequence data using SPAdes (Bankevich et al. Journal of computational biology, 19(5), 455-477. 2012 (http://doi.org/10.1089/cmb.2012.0021), the assembly was evaluated using QUASI (Gurevich et al. Bioinformatics. 2013 29(8): 1072-5. doi: 10.1093/bioinformatics/btt086.) The genome completeness and contamination were evaluated using CheckM (Parks et al., Genome Research 2015. 25: 1043-1055, doi: 10.1101/gr.186072.114).

As a result, the genome completeness exceeded 50% in half of all 44 of the analyzed single cell genomes, and exceeded 90% in four of them. Contamination was low, with an average of 1.9% (see Table 1).

TABLE 1

Results of evaluating the obtained single cell genomes

| Sample | Taxonomic classification | Completeness (%) | Contamination (%) |
|---|---|---|---|
| 1 | o_Lactobacillales | 97.31 | 4.66 |
| 2 | g_Lactobacillus | 96.86 | 2.25 |
| 3 | k_Bacteria | 96 | 0.67 |
| 4 | o_Lactobacillales | 94.48 | 0.2 |
| 5 | g_Lactobacillus | 89.32 | 7.98 |
| 6 | g_Lactobacillus | 87.77 | 3.24 |
| 7 | o_Lactobacillales | 85.54 | 0.27 |
| 8 | g_Lactobacillus | 85.32 | 1.79 |
| 9 | f_Bifidobacteriaceae | 82.99 | 4.2 |
| 10 | o_Lactobacillales | 74.33 | 2.17 |
| 11 | g_Lactobacillus | 74.02 | 0.65 |
| 12 | f_Bifidobacteriaceae | 72.85 | 3.68 |
| 13 | f_Bifidobacteriaceae | 69.06 | 6.26 |
| 14 | g_Bacillus | 68.53 | 3.36 |
| 15 | g_Bacillus | 65.3 | 1.73 |
| 16 | o_Bacteroidales | 64.73 | 2.39 |
| 17 | o_Clostridiales | 63.84 | 0.22 |
| 18 | g_Bacteroides | 63.04 | 5.5 |
| 19 | f_Bifidobacteriaceae | 61.51 | 2.79 |
| 20 | o_Lactobacillales | 60.97 | 0 |
| 21 | o_Bacteroidales | 56.13 | 1.69 |

TABLE 1-continued

Results of evaluating the obtained single cell genomes

| Sample | Taxonomic classification | Completeness (%) | Contamination (%) |
|---|---|---|---|
| 22 | f_Enterobacteriaceae | 53.45 | 2.42 |
| 23 | c_Bacilli | 50.81 | 4.03 |
| 24 | o_Clostridiales | 44.94 | 0.88 |
| 25 | k_Bacteria | 43.1 | 0.86 |
| 26 | k_Bacteria | 42.08 | 2.19 |
| 27 | k_Bacteria | 40.69 | 1.72 |
| 28 | k_Bacteria | 39.66 | 0 |
| 29 | o_Clostridiales | 37.75 | 0.68 |
| 30 | g_Clostridium | 36.89 | 0.88 |
| 31 | k_Bacteria | 36.36 | 2.3 |
| 32 | k_Bacteria | 29.98 | 0 |
| 33 | k_Bacteria | 27.59 | 0 |
| 34 | k_Bacteria | 27.04 | 1.72 |
| 35 | k_Bacteria | 24.14 | 1.72 |
| 36 | k_Bacteria | 21.55 | 3.45 |
| 37 | k_Bacteria | 20.69 | 2.07 |
| 38 | k_Bacteria | 7.55 | 0 |
| 39 | k_Bacteria | 7.02 | 1.75 |
| 40 | k_Bacteria | 6.9 | 0 |
| 41 | k_Bacteria | 5.17 | 0 |
| 42 | root | 0 | 0 |
| 43 | root | 0 | 0 |
| 44 | root | 0 | 0 |

When the above values were collated with the international standard in Minimum information about a single amplified genome (MISAG) (Bowers et al., Nature Biotechnology 2017 35(8): 725-731. doi: 10.1038/nbt.3893.4), single cell derived genome information acquired from a mouse stool was genome information that was evaluated to have medium to high quality. Genome information can also be obtained for gram positive bacteria by the approach in this Example.

In particular, 1.76 Mb of genome information with a completion ratio of 95% or greater was obtained for novel microbe closely related to the Firmicutes, Mollicutes, Mycoplasmatales. Furthermore, the obtained novel genomes were confirmed to be deficient of a lipid and amino acid synthesis system just like common Mollicutes microbes. This was inferred to be parasites for mice. On the other hand, a peptidoglycan synthesis system that is lacking in the vast majority of Mollicutes was conserved, so that it was expected that an attribute which is different from known Mollicutes microbes would be exhibited.

If it is assumed that 1 TB of sequence data is obtained in this experimental system, the rate of obtaining samples with a genome completeness exceeding 50% would be 5500 single cell genome data and 2200 microbial species. This is 5 to 17 fold compared to analysis of the same amount of data with conventional metagenomic sequencing (see FIG. 7).

In view of the above, the method of preparing the genome library 17 in this Example can randomly encapsulate microbes into mass produced gel capsules 11 and amplify the genomic DNA 14 individually by having the steps of: encapsulating cells of one or more microbes in the liquid microdroplets 3 for each single cell 4, at one cell per liquid droplet, by using a sample comprising the microbes; converting the liquid microdroplets 3 into gel to generate the gel capsule 11; immersing the gel capsule 11 in one or more types of bacteriolysis reagents 13 to lyse the cell 4 and retaining the genomic DNA 14, which has eluted out into the gel capsule 11, within the gel capsule 11; immersing the gel capsule 11 in the amplification regent 15 to amplify the genomic DNA 14 within the gel capsule 11; and sorting, separating, and collecting each gel capsule 11 with the genomic DNA 14 amplified. Lysis of the cell 4 and genome amplification can be performed sequentially with a simple operation. Hundreds of thousands to millions of parallel single cell genome amplification reactions can be materialized with an amount of reagent corresponding to a single reaction in a conventional method, so that the running cost can be dramatically reduced. Since only gel capsules 11 with progressed amplification can be selected for secondary amplification, unnecessary reaction operations targeting non-organism particles can be avoided. For the preparation of the single cell amplified genome library 17, amplification can be restarted with a sufficient amount of templates (pictogram equivalent) contained in the gel capsule 11, so that data quality degradation due to amplification of contamination molecules can be very effectively suppressed. Further, the single cell amplified genome library 17 is obtained at a volume in micrograms (amount corresponding to 1 million cells or more), thus overcoming the problem of yield in acquiring normal amplified genomes in conventional methods. The single cell amplified genome library 17 can be stored for an extended period of time under refrigerated or freezing conditions. Not only whole genome sequencing, but also re-analysis such as screening for a specific genetic sequence can be performed. Biological information of a precious environmental microbial sample being re-analyzable permanently as an amplified nucleic acid sample is a significant advantage in the still developing DNA sequencing technologies. Since not only the genome of microbe, but also information on plasmids retained within a cell can be concurrently analyzed, a substance producing gene or resistant gene on plasmids can also be detected.

The method of preparing the genome library 17 of this Example can wash and remove the bacteriolysis reagent 13, even when using a bacteriolysis reagent 13 comprised of a plurality of types of potent reagent groups that would inhibit a genome amplification reaction in a normal reaction, by having the step of removing the bacteriolysis reagent 13 and contaminant from the gel capsule 11 after immersing the gel capsule 11 in the bacteriolysis reagent 13. Furthermore, data quality degradation can be very effectively suppressed by concurrent removal of contamination molecules.

The method of preparing the genome library 17 of this Example can prepare liquid microdroplets 3 with a uniform diameter from preparing the liquid microdroplet 3 encapsulating the cell 4 by allowing the enteric microbial suspension 1 of the cell 4 to flow in the microchannel 2 and shearing the enteric microbial suspension 1 with the oil 10.

The method of preparing the genome library 17 of this Example can also increase the probability of the cell 4 being encapsulated in the liquid microdroplets 3, at one cell per liquid droplet, by configuring the diameter of the liquid microdroplets 3 to be 1 to 250 μm such as 20 to 200 μm.

The method of preparing the genome library 17 of this Example can also increase the probability of the cell 4 being encapsulated in the gel capsule 11, at one cell per gel capsule, by configuring the diameter of the gel capsule 11 to be 1 to 250 μm such as 20 to 200 μm.

The method of preparing the genome library 17 of this Example can readily prepare the gel capsule 11 by forming the gel capsule 11 from agarose, acrylamide, photocurable resin, PEG, gelatin, sodium alginate, matrigel, or collagen.

The method of preparing the genome library 17 of this Example can lyse a part of the cell 4 to harvest the genomic DNA 14 by selecting at least one type of the bacteriolysis reagent 13 from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12.

The method of preparing the genome library 17 of this Example can generate the gel capsule 11 from the liquid microdroplet 3 by the gel capsule 11 being a hydrogel capsule.

The method of preparing the genome library 17 of this Example can permanently re-analyze biological information of a precious environmental microbial sample as an amplified nucleic acid sample by being a method of manipulating a cell for library formation and whole genome analysis of a genome of a single cell derived from an uncultured microbe.

The preparation device 18 of the genome library 17 of this Example can randomly encapsulate microbes into mass produced gel capsules 11 and amplify the genomic DNA 14 individually by comprising: the liquid droplet preparation unit 19 for encapsulating the cells 4 in the liquid droplets 3, at one cell per liquid droplet; the gel capsule generation unit 20 for converting the liquid microdroplet 3 into gel to generate the gel capsule 11; the lysis reagent immersion unit 23 for immersing the gel capsule 11 in the bacteroplysis reagent 13; the removal unit 25 for removing a contaminant from the gel capsule 11; the amplification reagent immersion unit 27 for immersing the gel capsule 11 in the amplification reagent 15; and the sorting unit 29 for sorting the gel capsule 11 and housing the gel capsule 11 in the plate 16. Lysis of the cell 4 and genome amplification can be performed sequentially with a simple operation. Hundreds of thousands to millions of parallel single cell genome amplification reactions can be materialized with an amount of reagent corresponding to a single reaction in a conventional method, so that the running cost can be dramatically reduced. Since only gel capsules 11 with progressed amplification can be selected out for secondary amplification, unnecessary reaction operations targeting non-organism particles can be avoided. For the preparation of the single cell amplified genome library 17, amplification can be restarted with a sufficient amount of templates (pictogram equivalent) contained in the gel capsule 11, so that data quality degradation due to amplification of contamination molecules can be very effectively suppressed. Further, the single cell amplified genome library 17 is obtained at a volume in micrograms (amount corresponding to 1 million cells or more), thus overcoming the problem of yield in acquiring normal amplified genomes in conventional methods. The single cell amplified genome library 17 can be stored for an extended period of time under refrigerated or freezing conditions. Not only whole genome sequencing, but also re-analysis such as screening for a specific genetic sequence can be performed. Biological information of a precious environmental microbial sample being re-analyzable permanently as an amplified nucleic acid sample is a significant advantage in the still developing DNA sequencing technologies. Since not only the genome of microbe, but also information on plasmids retained within a cell can be concurrently analyzed, a substance producing gene or resistant gene on plasmids can also be detected.

The present invention is not limited to the Examples described above. Various modifications can also be made within the scope of the spirit of the invention. For example, other known containers can also be used as the tube 9 or plate 16. Further, samples such as seawater, soil, saliva, sputum, surgical detergent, blood, tissue harvested from the skin or oral cavity, and animal or plant tissue lysis solution can be used.

(Note)

As disclosed above, the present invention is exemplified by the use of its preferred embodiments. However, the present invention should not be interpreted to be limited to such embodiments. It is understood that the scope of the present invention should be interpreted based solely on the Claims. It is understood that an equivalent scope can be practiced based on the descriptions of the invention and common general knowledge from the specific descriptions in the preferred embodiments of the invention. It is also understood that any patent, any patent application, and any references cited herein should be incorporated herein by reference in the same manner as the contents are specifically described herein. The present application claims priority to Japanese Patent Application No. 2018-089259 (filed on May 6, 2018). It is understood that the entire content thereof is incorporated herein by reference.

INDUSTRIAL APPLICABILITY

The present invention can be used in the fields of biological research, medicine, environment, healthcare, and the like.

REFERENCE SIGNS LIST

1 Enteric microbial suspension
2 Microchannel
3 Liquid microdroplet (liquid droplet)
4 Single cell of mouse enteric microbe
5 First channel
6 Second channel
7 Third channel
8 Fourth channel
9 Tube
10 Oil
11 Gel capsule
12 Aqueous layer
13 Bacteriolysis reagent
14 Genomic DNA (polynucleotide)
15 Amplification reagent
16 Plate (housing container)
17 Single cell amplified genomic library
18 Preparation device
19 Liquid droplet preparation unit
20 Gel capsule generation unit
21 Cooling unit
22 UV ray irradiation unit
23 Lysis reagent immersion unit
24 Lysis reagent infusion unit
25 Removal unit
26 Centrifugal washing unit
27 Amplification reagent immersion unit
28 Amplification reagent infusion unit
29 Sorting unit
30 Flow cytometer
31 Container

SEQUENCE LISTING FREE TEXT

SEQ ID NO: 1: Forward primer
SEQ ID NO: 2: Reverse primer

The invention claimed is:

1. A method of amplifying a polynucleotide in a cell or a cell-like construct, comprising the steps of:
encapsulating two or more cells or cell-like structures in liquid droplets, at one cell or construct unit per liquid droplet, by using a sample comprising the cells or cell-like structures;
converting the liquid droplets into gel to generate a gel capsule;
immersing the gel capsule in one or more types of lysis reagents to lyse the cells or cell-like structures, wherein a polynucleotide in the cells, which has eluted out into the gel capsule, is retained in the gel capsule with a substance binding to the polynucleotide removed; and
contacting the polynucleotide with an amplification reagent to amplify the polynucleotide within the gel capsule while maintaining a gelatinous state.

2. The method of claim 1, wherein the cells comprise a microbial cell.

3. The method of claim 2, wherein the lysis reagent comprises lysozyme, achromopeptidase, protease K, sodium dodecyl sulfate, and potassium hydroxide.

4. The method of claim 1, wherein the lysis reagent and a contaminant are removed from the gel capsule after immersing the gel capsule in the lysis reagent.

5. The method of claim 1, wherein the liquid droplets encapsulating the cells or cell-like structures are prepared by allowing a suspension of the cells or cell-like structures to flow in a microchannel and shearing the suspension with oil.

6. The method of claim 1, wherein a diameter of the liquid droplets is 1 to 250 μm.

7. The method of claim 1, wherein a diameter of the gel capsule is 1 to 250 μm.

8. The method of claim 1, wherein the gel capsule is formed from agarose, acrylamide, photocurable resin, PEG, gelatin, sodium alginate, matrigel, or collagen.

9. The method of claim 1, wherein at least one type of the lysis reagent is selected from the group consisting of lysozyme, labiase, yatalase, achromopeptidase, protease, nuclease, zymolyase, chitinase, lysostaphin, mutanolysin, sodium dodecyl sulfate, sodium lauryl sulfate, potassium hydroxide, sodium hydroxide, phenol, chloroform, guanidine hydrochloride, urea, 2-mercaptoethanol, dithiothreitol, TCEP-HCl, sodium cholate, sodium deoxycholate, Triton X-100, Triton X-114, NP-40, Brij-35, Brij-58, Tween 20, Tween 80, octyl glucoside, octyl thioglucoside, CHAPS, CHAPSO, dodecyl-β-D-maltoside, Nonidet P-40, and Zwittergent 3-12.

10. The method of claim 1, wherein the gel capsule is a hydrogel capsule.

11. The method of claim 1, wherein the step of amplifying is performed by an isothermal strand displacement amplification reaction.

12. The method of claim 1, wherein a gel liquid droplet shape is maintained in the amplification step.

13. The method of claim 1, wherein the state wherein the substance binding to the polynucleotide is removed is a state where a DNA binding protein is removed.

14. The method of claim 1, further comprising the step of sequencing a nucleic acid sequence in the amplified polynucleotide.

15. A method of preparing a genome library, comprising the step of sorting, separating, and collecting each gel capsule with the polynucleotide amplified by the method of claim 1.

16. A method of genome sequencing of a cell at a single-cell level, comprising the step of genomic DNA sequencing of the cell from a polynucleotide amplified by the method of claim 1.

17. A method of genome sequencing of a cell at a single-cell level, comprising the steps of:
encapsulating two or more cells or cell-like structures in liquid droplets, at one cell or construct unit per liquid droplet, by using a sample comprising the cells or cell-like structures;

converting the liquid droplets into gel to generate a gel capsule;

immersing the gel capsule in one or more types of lysis reagents to lyse the cells or cell-like structures, wherein a polynucleotide in the cells, which has eluted out into the gel capsule, is retained in the gel capsule with a substance binding to the polynucleotide removed;

contacting the polynucleotide with an amplification reagent to amplify the polynucleotide within the gel capsule while maintaining a gelatinous state; and determining a whole sequence of a genomic DNA of the cells from the amplified polynucleotide, wherein the cells comprise a microbial cell, wherein the lysis reagent comprises lysozyme, achromopeptidase, protease K, sodium dodecyl sulfate, and potassium hydroxide;

wherein the state where the substance binding to the polynucleotide is removed is a state where a DNA binding protein is removed, and wherein the amplification step is performed by an isothermal strand displacement amplification reaction.

18. A device for amplifying a polynucleotide in a cell, comprising:

a liquid droplet preparation unit for encapsulating cells or cell-like structures in liquid droplets at one cell or construct unit per liquid droplet;

a gel capsule generation unit for converting the liquid droplets into gel to generate a gel capsule;

a lysis reagent immersion unit for immersing the gel capsule in a lysis reagent, wherein the lysis reagent immersion unit is configured so that a polynucleotide in the cells, which has eluted out into the gel capsule, is retained in the gel capsule, with a substance binding to the polynucleotide removed, upon lysis;

a removal unit for removing a contaminant from the gel capsule; and an amplification reagent immersion unit for immersing the gel capsule in an amplification reagent, wherein the amplification reagent immersion unit is configured so that a gelatinous state is maintained for the gel capsule during amplification.

19. The device of claim 18 further characterized in genome sequencing of a cell at a single-cell level, further comprising a sequencing unit for sequencing a nucleic acid sequence in a polynucleotide amplified by the amplification reagent immersion unit.

20. The device of claim 18 further characterized in preparing a genome library, further comprising a sorting unit for sorting the gel capsule and housing the gel capsule in a housing container.

21. The device of claim 18, wherein the liquid droplet preparation unit comprises a microchannel.

* * * * *